United States Patent [19]
Foster et al.

[11] Patent Number: 5,117,521
[45] Date of Patent: Jun. 2, 1992

[54] CARE CART AND TRANSPORT SYSTEM

[75] Inventors: L. Dale Foster, Brookville; John W. Reuhl, Batesville, both of Ind.

[73] Assignee: Hill-Rom Company, Inc., Batesville, Ind.

[21] Appl. No.: 524,038

[22] Filed: May 16, 1990

[51] Int. Cl.⁵ ............................................... A47G 21/00
[52] U.S. Cl. ........................................ 5/510; 5/503.1; 5/658; 280/481; 248/129
[58] Field of Search ............... 5/508, 510, 503, 60; 280/33.991, 481, 47.34; 248/129; 296/20

[56] References Cited

U.S. PATENT DOCUMENTS

| | | |
|---|---|---|
| D. 260,816 | 9/1981 | Zissimopoulos et al. |
| 1,290,809 | 1/1919 | Truax |
| 2,470,524 | 5/1949 | Scudder |
| 2,607,929 | 8/1952 | Balluff ........................... 296/20 |
| 2,673,771 | 3/1954 | Krewson |
| 2,696,963 | 12/1954 | Shepherd |
| 3,524,512 | 8/1970 | Voeks ........................... 280/33.991 |
| 4,225,104 | 9/1980 | Larson |
| 4,262,872 | 4/1981 | Kodet |
| 4,511,158 | 4/1985 | Varga et al. |
| 4,584,989 | 4/1986 | Stith ........................... 296/210 |
| 4,592,104 | 1/1986 | Foster ........................... 5/60 |
| 4,600,209 | 7/1986 | Kerr |
| 4,729,576 | 3/1988 | Roach ........................... 5/508 |
| 4,795,122 | 1/1989 | Petre |
| 4,905,944 | 3/1990 | Jost ........................... 248/129 |
| 4,945,592 | 8/1990 | Sims ........................... 248/129 |
| 4,966,340 | 10/1990 | Hunter ........................... 5/503 |

FOREIGN PATENT DOCUMENTS 2812037  9/1979  Fed. Rep. of Germany .......... 5/503

Primary Examiner—Rodney M. Lindsey
Assistant Examiner—F. Saether
Attorney, Agent, or Firm—Wood, Herron & Evans

[57] ABSTRACT

A care cart and a hospital bed having mating bases to permit the care cart to nest with the hospital bed. The combination of cart and bed can be rolled from place to place to transport the patient and the cart can be removed from the bed while maintaining the life support systems connected to the patient while the patient is transferred to another patient support.

7 Claims, 4 Drawing Sheets

CARE CART AND TRANSPORT SYSTEM

BACKGROUND OF THE INVENTION

This invention relates to a care cart for life support systems and a system for transporting a patient and for transferring a patient from his or her transport bed to another patient support surface such as an X-ray table.

When a patient is in intensive care or critical care, the patient is usually connected to a number of life support systems as, for example, infusion pumps for delivering IV solutions, oxygen, suction, heart monitoring, and the like. Such patients need to be transported, with their life support systems, from the patient's room to other stations in the hospital where diagnostic or treating equipment is provided such as X-ray, CAT scan and MRI. There, the patient must be transferred from the transporting bed to the table of the diagnostic/treating equipment. The life support systems must remain attached but be out of the way of the functioning of the personnel and equipment.

These needs have been known. One attempt to meet the need has been to provide a wheeled tree, so to speak, on which the life support equipment is mounted. The tree stays by the patient's bed in the patient's room, but when the patient is transported to another location, an attendant pushes the tree along with the bed which is pushed by another attendant.

Cleveland Clinic Foundation has developed another system as described in its U.S. Pat. No. 4,795,122. An overhead boom is provided in the patient's room and a detachable IV rack is mounted on the boom. The swinging capability of the boom enables the nursing staff to move the IV rack out of the way when necessary to attend to the patient. A transport bed that has a mating connection to the IV rack is adapted to receive the IV rack as it is lowered from the boom toward the patient's bed. The IV rack is then separated from the boom, enabling it to be carried with the patient to the site of the diagnostic/treating equipment. At that site, a similar boom is provided to grasp the IV rack and lift it off the bed so that it is out of the way of the transfer and treatment of the patient.

BRIEF SUMMARY OF THE INVENTION

An objective of the present invention has been to provide an improved system for supporting a rack for life support systems adjacent a patient while the patient is in the hospital room, while the patient is being transported to another area, and while the patient is shifted to another support such as an X-ray table.

Another objective of the present invention has been to eliminate the need for a rack-supporting boom at every station where the patient is transferred from his or her bed.

Another objective of the present invention has been to eliminate the need for a separate cart that must be rolled, by an attendant, alongside the patient's transport bed when the patient is transported from one site to another.

Still another objective of the present invention has been to eliminate the need for a transport bed specially designed to receive a life support system. In this latter regard, the inventor here has described, in U.S. Pat. No. 4,985,946, a hospital bed having a specific Y-shaped base that facilitates the use of the C-arm mobile X-ray unit. That bed has two widths: wide, for normal hospital room patient support, and narrow, for patient transport.

It is contemplated that that same base will be employed for a whole family of hospital beds. It will be seen hereafter how that base cooperates with the care cart of the present invention to provide the nesting relationship that achieves the objectives of the invention.

The foregoing objectives of the present invention are attained by providing a self-supporting care cart having a mating configuration with the end of a bed. The care cart can be docked at the end of the bed and latched there so that the bed and cart can be moved as one in transporting a patient from place to place. At the patient's bedroom, the rack can be transferred to the cart in a manner similar to the transfer of the rack to a bed as depicted in U.S. Pat. No. 4,795,122.

At the site of the equipment to which the patient must be transferred, the care cart can be separated from the bed and moved to an out-of-the-way location where it does not interfere with the activities of the attending personnel or of the operation of the equipment itself and without detaching life support systems from the patient.

More specifically, the invention contemplates a patient's bed having a base of a Y configuration, one end being formed of spaced branches with casters at the ends of the branches. The care cart has a narrow front end and is adapted to slide between the outspread branches of the bed base to nest there when the bed is moved from one site to another. In the nesting attitude, the care cart adds very little to the profile or footprint of the bed, that is, the floor space that it must occupy. Further, the care cart moves as one with the bed as the bed is moved from one site to another, thus requiring a minimum of personnel to transport the patient from site to site.

BRIEF DESCRIPTION OF THE DRAWINGS

The several objectives and features of the invention will become more readily apparent from the following detailed description taken in conjunction with the accompanying drawings in which.

DETAILED DESCRIPTION OF THE INVENTION

Figure 1:
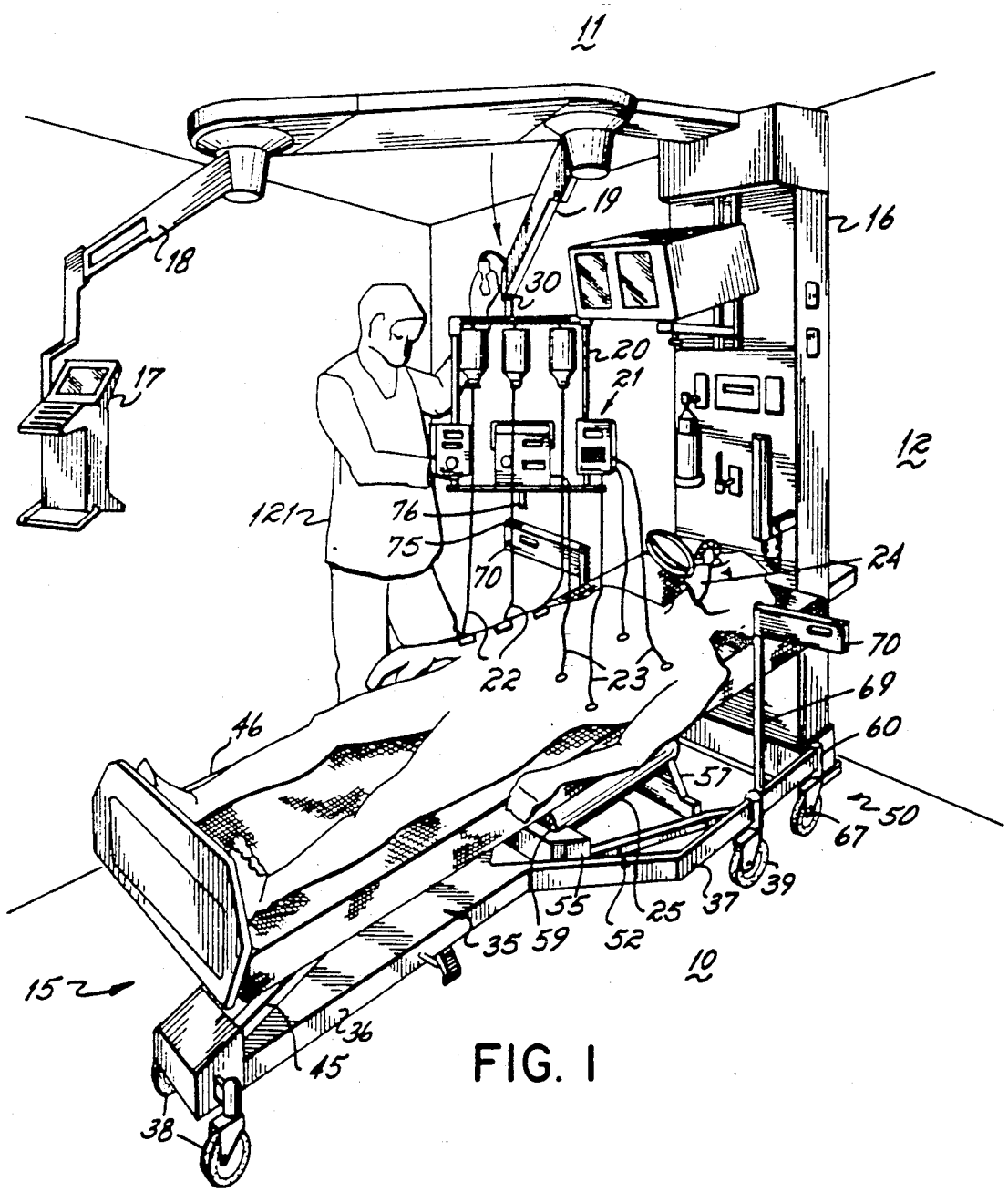
FIG. 1 is a perspective view of a hospital room containing the elements of the system of the present invention.

In FIG. 1 there is disclosed a hospital room generally of the type depicted in copending application Ser. No. 07/309,886, filed Feb. 14, 1989. The room has a floor 10, a ceiling 11 and walls 12. A patient's bed 15 is positioned on the floor adjacent a power column 16. Suspended from the ceiling is a computer terminal 17 on a boom 18. Another boom 19 carries an rack 20. The rack 20 has various life support systems all indicated generally at 21 and all attached to the patient by fluid conducting tubes 22 or electric conductors 23. Oxygen is supplied to a mask 24 from a canister 25.

The rack 20 has a detachable connection at 30 to the boom 18. One example of the detachable connection is depicted in U.S. Pat. No. 4,795,122, the disclosure of which is fully incorporated herein by reference. Either the boom 19 can be raised and lowered as by means of a counterweight system or, alternatively, a pneumatic connection at 30, which can raise the rack 20 and lower it, is mounted on the end of the boom. The rack thus is adapted to be swung to either side of the patient on a pivot axis that passes through the center of the bed at approximately the chest of the patient, as disclosed in application Ser. No. 144,188, filed Jan. 15, 1988 now U.S. Pat. No. 4,811,435.

The bed 15 has a base 35. The base 35 is generally Y-shaped, having a stem section 36 and diverging branches 37. Casters 38 are mounted on the front end and casters 39 are mounted on the branches at the rear end of the bed.

Cantilevered up from the front end of the bed is a parallelogram support linkage 45. A patient support 46 is mounted on the support linkage. A piston and cylinder 47 (FIG. 2) maintains the patient support at a desired level that may be varied as needed for the patient's care, transport and transfer from one support to another. The bed 15, for transport purposes, is preferably of the type depicted in U.S. Pat. No. 4,985,946, the bed being adapted to be converted from a relatively wide patient support of conventional dimension of 42 inches to a narrow support with a width dimension of approximately 36 inches for movement in tight corners, elevators and the like.

A care cart 50 (see also FIGS. 2 an 3) is shown docked within the diverging branches 37 of base 35. Referring particularly to FIG. 3, the care cart has a base 52 which is narrow at its front end 53 and has two casters 54 supporting the front end. A docking block 55 is mounted on the front end. Two diverging frame members 56 project rearwardly from the docking block. They are connected together by a transverse brace 57 which has an arcuate recess 58. A cooperating operating recess 59 in the docking block 55 provides a receptacle for the oxygen canister 25. Each frame member 56 has a swinging foot 60 pivotally mounted at its rear end. Each swinging foot carries a caster 67 pivotally mounted on an axis 68 to the foot. The foot itself carries a vertical post 69 on the pivot axis of the foot to the frame member 56. Arms 70 are fixed to the post 69. Swinging of the arms 70 and post 69 about the pivot axis 61 carries the feet 60 and casters 67 with them so that the arms remain aligned with the feet.

Each arm 70 has an upwardly-facing socket 75. The rack 20 has a depending stud 76 (FIGS. 1 and 2) which is received in the socket 75 to shift the support of the rack 20 from the boom 18 to the care cart.

By providing the swinging arms 70, the position of the rack with respect to the bed can be changed. By mounting the arms 70 in alignment with the feet 50 and by providing a rigid interconnection of arms through the post 69 to the feet 60, when the arms swing to an outboard position, for example, the weight of the rack mounted on the arms continues to be supported directly over the caster pivot axis 68, thus maintaining the stability of the care cart.

Figure 2:
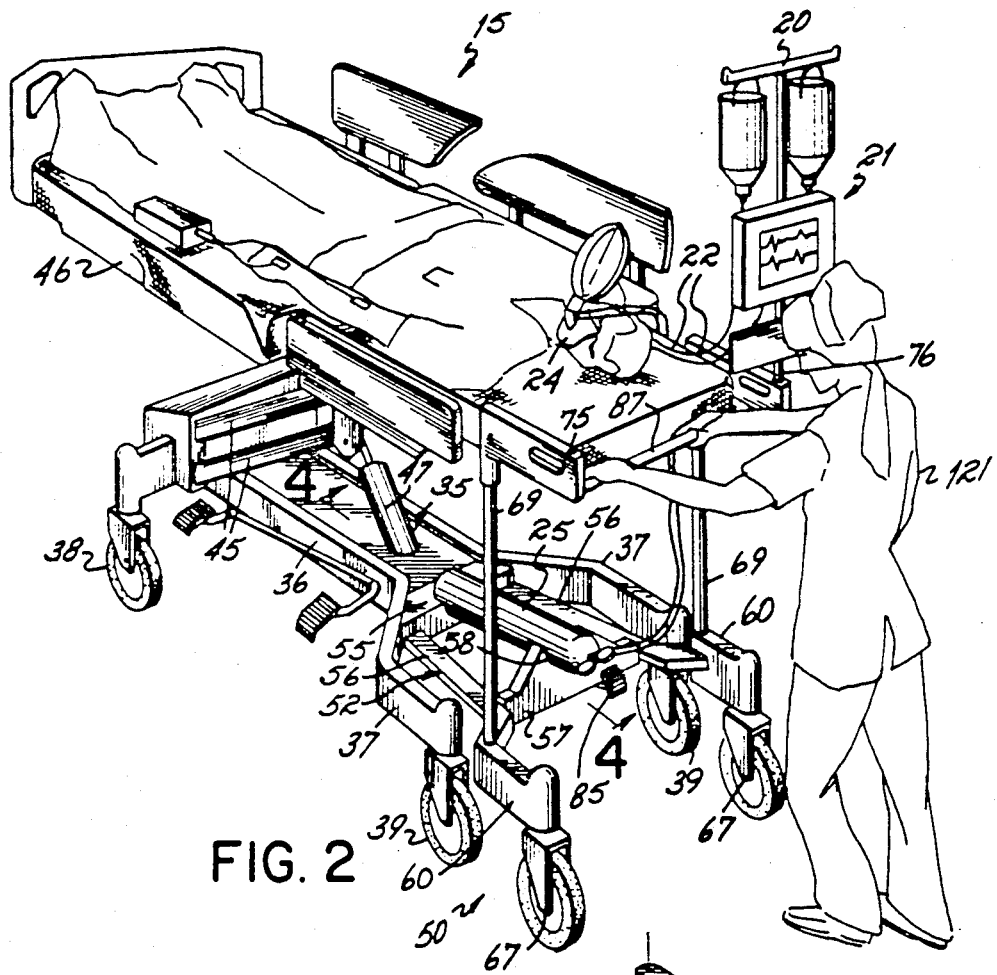
FIG. 2 is a perspective view illustrating the transport of a patient.
Figure 3:
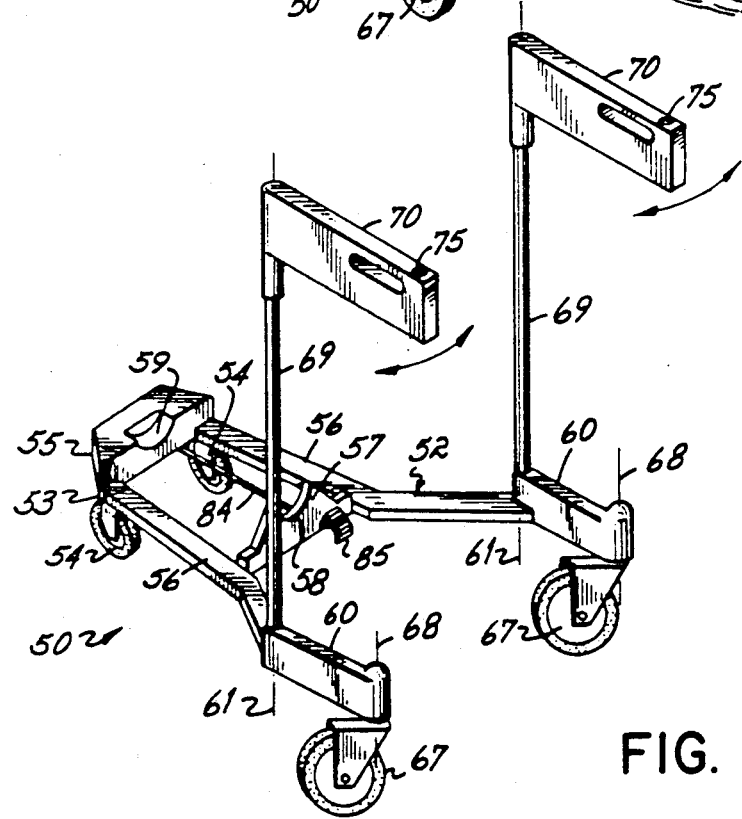
FIG. 3 is a perspective view of the care cart of the present invention.
Figure 4:
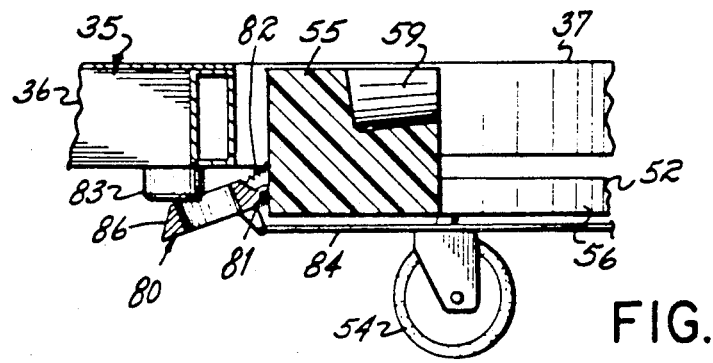
FIG. 4 is a cross-sectional view taken along lines 4—4 of FIG. 2 illustrating the latching mechanism that joins the cart to the bed.

Referring particularly to FIGS. 2, 3 and 4, the docking block 55 has a ring 80 mounted to it on a pivot axis 81. A tension spring 82 is connected between the ring 80 and the block 55 to urge the ring in an upward position. The bed base 35 has a depending post 8 which is captured in the ring 80. An elongated rod 84 is connected to the ring and is operated by a foot pedal 85 mounted on the brace 57 to manipulate the ring 80 to disengage it from the post 83. In docking the cart, the ring is cammed downwardly by the engagement of a surface 86 with the post 83 to cause the ring to receive the post automatically as the cart is pushed into a docking position with respect to the bed.

The dimension between the diverging branches 37 of the bed base is about 25". The transverse dimension of the cart is slightly less than that in order to permit the cart to be received between the diverging branches 37.

The arms 70 and the swinging feet 60 project rearwardly from under the patient's support surface or sleep surface deck. When bumpering, such as is depicted at 87 (in FIG. 1), is mounted on the sleep surface, the projection of the arms and feet beyond the sleep surface is only about 5". The point is that the invention provides for a cart of significant dimension to carry the life support systems rack, but when the cart is nested in its operative position within the bed base 35, the cart adds very little to the profile or footprint of the bed.

Figure 5:
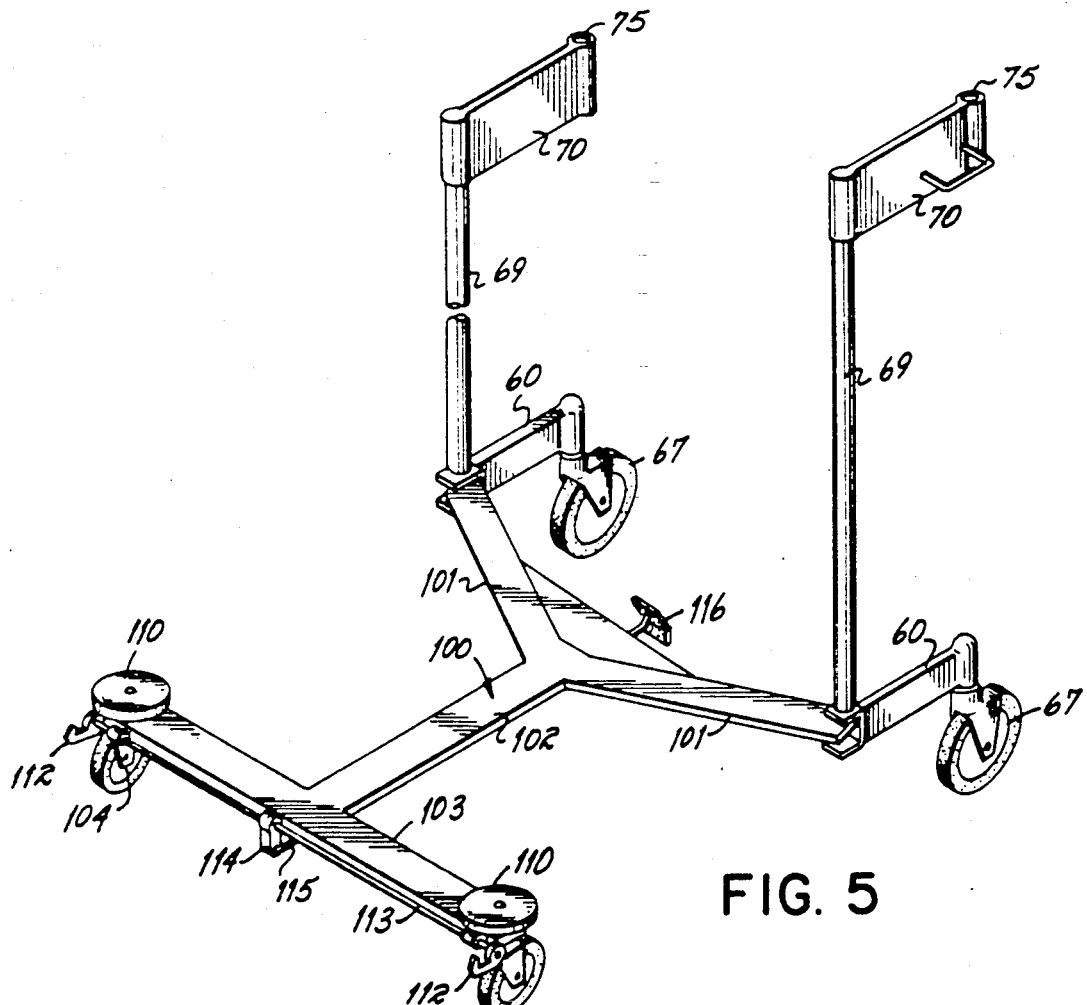
FIG. 5 is a perspective view of an alternative care cart.
Figure 7:
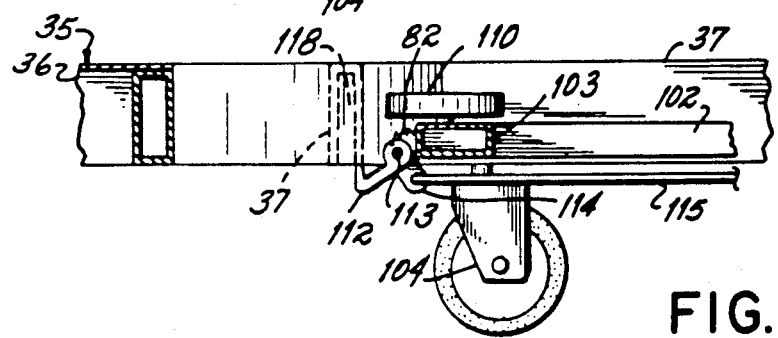
FIG. 7 is a cross-sectional view taken along lines 7—7 of FIG. 6.
Figure 6:
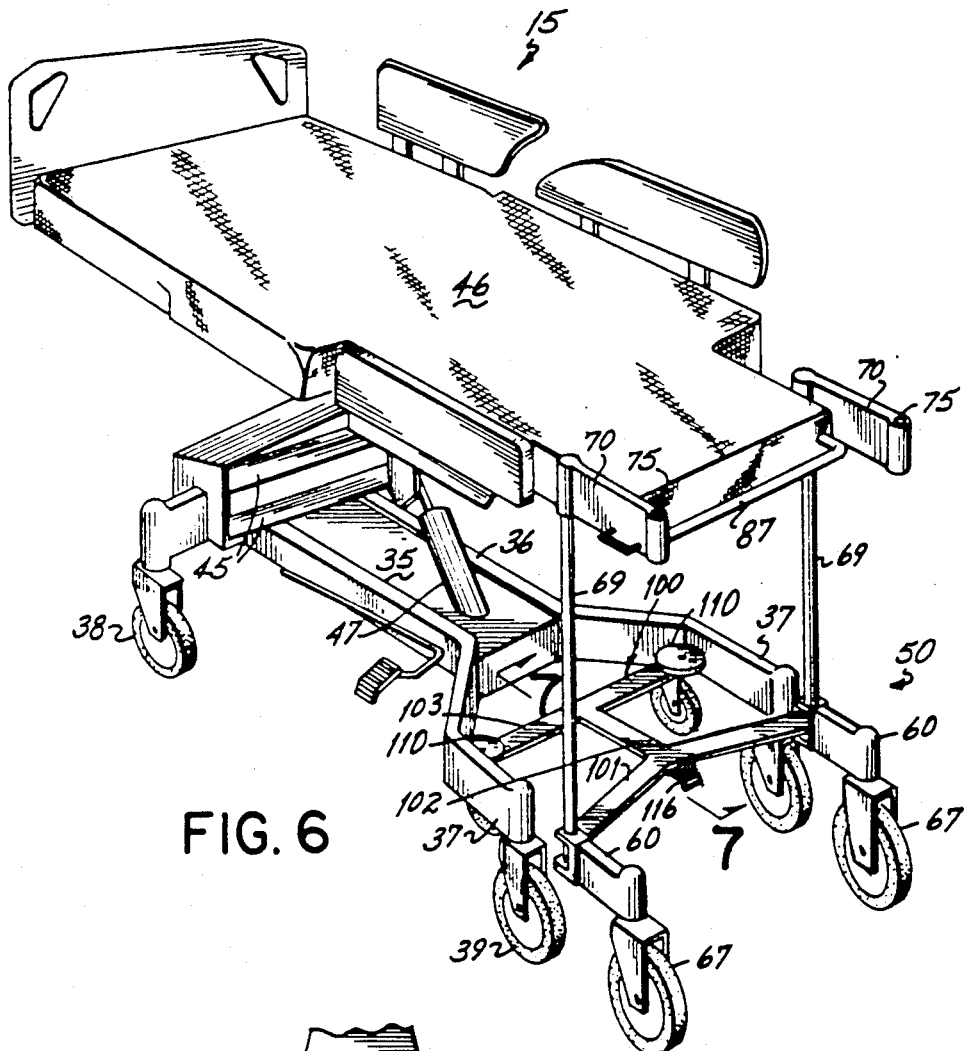
FIG. 6 is a perspective view of the alternative care cart docked with respect to the bed.

An alternative form of the cart is illustrated in FIGS. 5-7. The principal difference between the cart of FIG. 5 and the cart of FIG. 3 is in the front docking surface. In FIG. 5, the cart has a base 100 with diverging frame members 101 at the rear end. The diverging members 101 are connected by a stem 102 to a crossbar 103. The crossbar carries casters 104 and the diverging members 101 carry swinging feet 60, vertical posts 69 and swinging arms 70 of the embodiment of FIG. 3.

The crossbar 103 has a circular disc-like bumper 110 at each end. As shown in FIG. 6, the bumpers 110 cooperate with the bed diverging frame branches 37 to assist in guiding the cart into docking position. The crossbar 103 carries a pair of latches 112 which are mounted on a transverse rod 113. The transverse rod is mounted on an arm 114 pivoted to the crossbar and operated by a longitudinal rod 115 connected to a foot panel 116. As shown in FIG. 7, the latch elements 112 are adapted to engage into the interior 118 of inverted U-shaped channels that form the diverging branches 37.

In the operation of the invention, a patient is connected to multiple tubes and conductors providing life support and monitoring functions. The principal instruments for performing those functions are mounted on the rack 20 which is in turn detachably connected to swinging boom 18.

Figure 8:
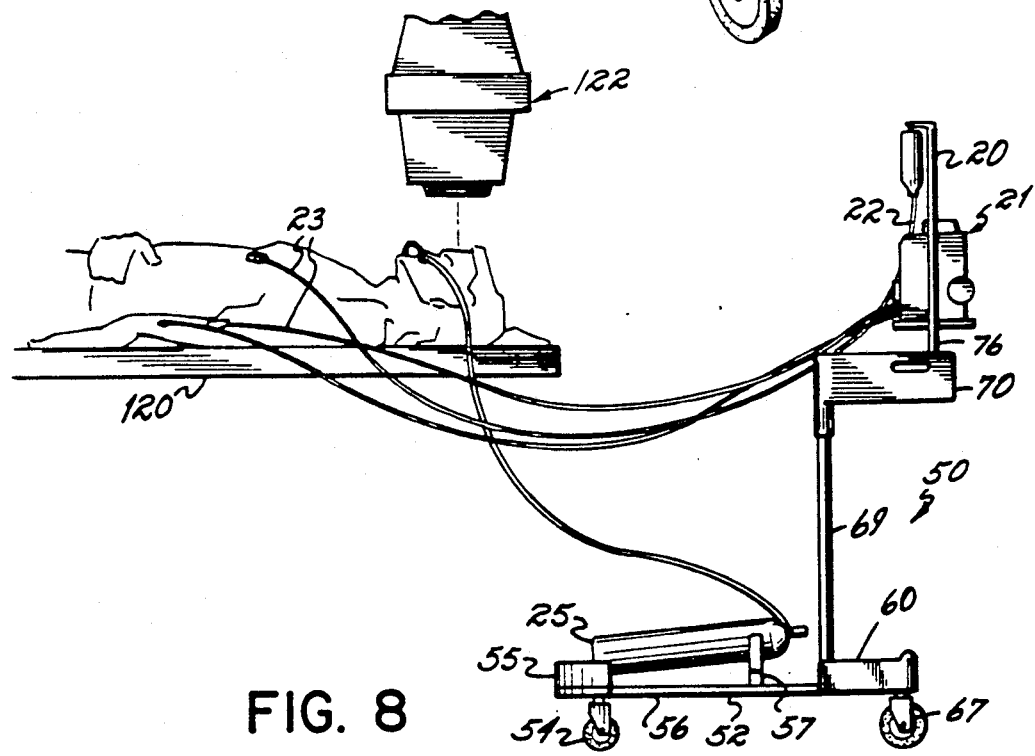
FIG. 8 is a diagrammatic side elevational view of the cart and diagnostic/treatment equipment.

The patient is to be moved to a new site such as to an X-ray table 120 shown in FIG. 8. An attendant, indicated at 121 (shown in FIG. 1), by swinging the boom 18, aligns the stud 76 with the hole 75 on one of the arms of the care cart. The rack is slowly lowered until the stud is seated in the arm 70, thereby providing full support for the rack. The rack is then detached from the boom 18.

The arms of the cart 50 are preferably swung directly rearwardly, as shown in FIG. 3. The cart has previously been docked in a nested position wherein the cart is disposed between the diverging branches 37 of the base of the bed, as is shown in FIGS. 1 and 2. The cart is latched there. The attendant pushes the bed from the site of the patient's bedroom to the site of an X-ray machine 120, for example. Note, from viewing FIG. 2, that this is a one person operation. At the X-ray station, (it could be any other diagnostic/treatment station) the patient is transferred from the bed support surface 46 to a table 120. The bed 15 is moved out of the way by first detaching the care cart so that as the bed is removed, the nesting relationship is discontinued. The care cart is then shifted to a position, as for example at the head end of the table 120, where it is out of the way of the attending personnel and of the diagnostic/treatment machinery 122.

The patient having been treated, the patient is transferred back to the bed supporting surface 46. The care cart is docked and latched in the nesting configuration of FIG. 2 The bed is then rolled to the patient's room, as shown in FIG. 1.

The embodiment of FIG. 5 may be preferred over the embodiment of FIG. 3 in that it permits the cart to be nested under a bed and pivoted away from the bed utilizing a smaller area than does the embodiment of FIG. 3. Referring to FIG. 6, for example, with no substantial backing out of the care cart 50, the cart can be pivoted to either side of the bed with the leg of the bed frame branch 37 hooking into the space between the crossbar 103 and the diverging member 101. The introduction of the cart into the bed has the same minimal space requirement. The crossbar 103 simply hooks around diverging branch 37 of the bed and the cart is then swung into position as depicted in FIG. 6. This may be particularly useful in hospital rooms where there is a limited amount of space for moving the head of the bed away from the wall before the care cart can be nested into the rear end of the bed. Because of the different forward construction of the care cart of FIG. 3, the nesting with respect to the bed requires more space than does the cart of FIG. 5.

Both carts have smaller front wheels than rear wheels. The difference is such as to lower the front end of each cart s that it rolls under the rear structure of a similar cart, thus permitting the carts themselves to be nested together for the purpose of minimal space requirement in storage.

From the above disclosure of the general principles of the present invention and the preceding detailed description of a preferred embodiment, those skilled in the art will readily comprehend the various modifications to which the present invention is susceptible. Therefore, we desire to be limited only by the scope of the following claims and equivalents thereof:

We claim:

1. A hospital patient care cart for receiving and carrying equipment connected to a patient comprising:
   a base, casters mounted on said base,
   a support for an IV rack projecting upwardly from said base, a receptacle for a gas cannister mounted on said base,
   said base having a wide rear end supported on casters and a narrow front end supported on casters, said narrow front end adapted to project between branches of a Y-shaped base for a hospital bed,
   and a latching mechanism on the front end of said cart base for connection to said bed base to permit said cart to be joined to said bed base and rolled from place to place as a unit.

2. A care cart as in claim 1 in which said support comprises:
   a post projecting upwardly from each side of said rear end, each post having a laterally projecting arm, each arm having a receptacle to receive a rack.

3. A care cart as in claim 2 further comprising:
   rearwardly-projecting feet and casters pivotally mounted on the rear end of said base,
   said arms overlying said feet and being rigidly interconnected to said feet through said vertical posts, whereby, as said rack is swung, on an arm, to a lateral position with respect to said cart, said arms and feet will swing laterally together to provide support for said rack by said caster directly below it.

4. Apparatus comprising:
   a hospital bed,
   a care cart including a support for receiving an IV rack and a receptacle for a gas cannister,
   means forming structure on said bed and cart permitting said bed and care cart to nest and move as a unit and to separate when desired
   said hospital bed having a base that includes rear diverging branches casters mounted on the ends of the branches,
   said care cart having a front end that is narrow and passes between said branches to nest between said branches.
   and means to latch said care cart to said bed base.

5. Apparatus as in claim 4 in which said care cart has a crossbar at its front end,
   bumpers on the ends of said crossbar and engageable with said diverging branches of said bed base to guide said care cart into nesting position with respect to said bed.

6. Apparatus comprising:
   a hospital bed, a base frame supporting said bed and having a recess in one end of said base frame,
   a care cart including a support for receiving an IV rack and a receptacle for a gas cannister, a base for said care cart having a narrow front end that is projectable into said bed base,
   said care cart base nesting in said bed base for transport from room to room as a unitary structure, said care cart being separable from said bed to provide room for the performance of procedures requiring access to the nested position of said cart.

7. Apparatus comprising:
   a hospital bed having a base that includes rear diverging branches, casters mounted on the ends of said branches,
   a care cart having a front end that is narrow and passes between said branches to nest between said branches,
   said cart having a docking block to which a latching ring is pivotally mounted,
   and said bed base having a depending post to be received in said ring to latch said cart to said bed.

* * * * *